United States Patent [19]

Carriere

[11] 4,160,388
[45] Jul. 10, 1979

[54] POWER MEASURING APPARATUS FOR ULTRASONIC TRANSDUCERS

[75] Inventor: Victor Carriere, London, Canada

[73] Assignee: Bach-Simpson Limited, London, Canada

[21] Appl. No.: 916,474

[22] Filed: Jun. 19, 1978

[51] Int. Cl.² .................................... G01N 29/00
[52] U.S. Cl. ........................................ 73/646
[58] Field of Search ............ 73/1 DV, 646, 645, 596; 340/5 C

[56] References Cited

U.S. PATENT DOCUMENTS 2,762,447  9/1956  Cady ........................................ 73/646
3,915,017 10/1975  Robinson ............................. 73/1 DV

OTHER PUBLICATIONS

Wells et al., "Milliwatt Ultrasonic Radiometry," *Ultrasonics*, Jul./Sep. 1964, pp. 124–128.

*Primary Examiner*—Stephen A. Kreitman
*Attorney, Agent, or Firm*—McDougall, Hersh & Scott

[57] ABSTRACT

A measuring apparatus employs a target vane suspended from a movable arm and disposed in a water bath. The transducer under test is arranged to direct its energy at the vane. An electric nulling circuit maintains the arm in its initial position. The current required to do so is a measure of the power of the transducer. An acoustic trap is provided to insure accurate measurement.

10 Claims, 4 Drawing Figures

POWER MEASURING APPARATUS FOR ULTRASONIC TRANSDUCERS

BACKGROUND OF THE INVENTION

This invention relates to the field of testing and measuring apparatus. More specifically, it relates to the field of apparatus for measuring the power output of ultrasonic transducers. Although such transducers find wide application in industry, they are particularly useful in the medical field as a diagnostic tool. In that context the transducer produces ultrasonic waves which are projected into the human body. The intensity of the waves must be accurately maintained to insure that no physiological damage is done to the patient. Thus, it is necessary to periodically calibrate transducers and to measure their transmitted acoustic power.

Measurement devices for ultrasonic transducers are known. See, for example, the references discussed in the prior art statement which follows. However, those devices have not been entirely satisfactory in accuracy or in their ability to measure low transducer power output on the order of 300 mircowatts. Typically, such devices employ mechanical balance type schemes with the attendant inaccuracies due to the friction of the fulcrum, the weight of wires, etc., which thereby limit the accuracy of the testing devices. It is accordingly an object of the present invention to provide an improved power measuring apparatus for ultrasonic transducers which has a greater range and sensitivity than prior devices.

Another object of the present invention is to provide a measuring apparatus of the type indicated employing a tautband d'Arsonval meter movement as part of the transducer target suspension.

Another object of the invention is to provide an automatic restoring circuit for maintaining the target at the null point, which circuit provides a direct meter reading of the current required to maintain the null, which reading may be calibrated to correspond to the power output of the transducer.

Other objects and advantages of the invention will be apparent from the remaining portion of the specification.

PRIOR ART STATEMENT

In accordance with the provisions of 37 CFR $1.97, applicant advises that the following are the closest prior art references of which he is aware: "Milliwatt Ultrasonic Radiometry," P.N.T. Wells et al, "Ultrasonics," July/September 1964, page 124. and U.S. Pat. No. 3,915,017 to Robinson. Wells et al teach the measurement of transducer power by immersing the transducer in a tank filled with water. The energy from the transducer strikes a target suspended by a wire and is then reflected into an ultrasonic trap. The distance the target is deflected provides an indication of the power of the transducer. The necessary correction factors for the forces due to the surface tension of the water and target bouyancy, appear to be much larger than the forces being measured.

The patent to Robinson discloses a transducer measuring apparatus employing a balance beam construction. A target 2 is provided on one end of a beam 12, a set of electromagnetic coils being suspended from the other end of the beam. The beam is balanced near its mid-point on a jeweled fulcrum 14. A circuit is provided (FIG. 6) for maintaining a null point by selectively energizing coils 22 and 24. The amount of energizing current required to maintain the null point is a measure of the energy output of the transducer under test.

SUMMARY OF THE INVENTION

The present invention overcomes the deficiences of the prior art just described and permits accurate transducer output measurement down to energies on the order of 300 microwatts. A target of neutral buoyancy is provided in a water bath suspended from an arm which forms the movable portion of a tautband d'Arsonval meter movement. A circuit is provided to maintain the target in the null or original position. The electric current required to maintain the null before and during operation of the target is compared to accurately determine the transducer output energy.

DETAILED DESCRIPTION

Figure 1:
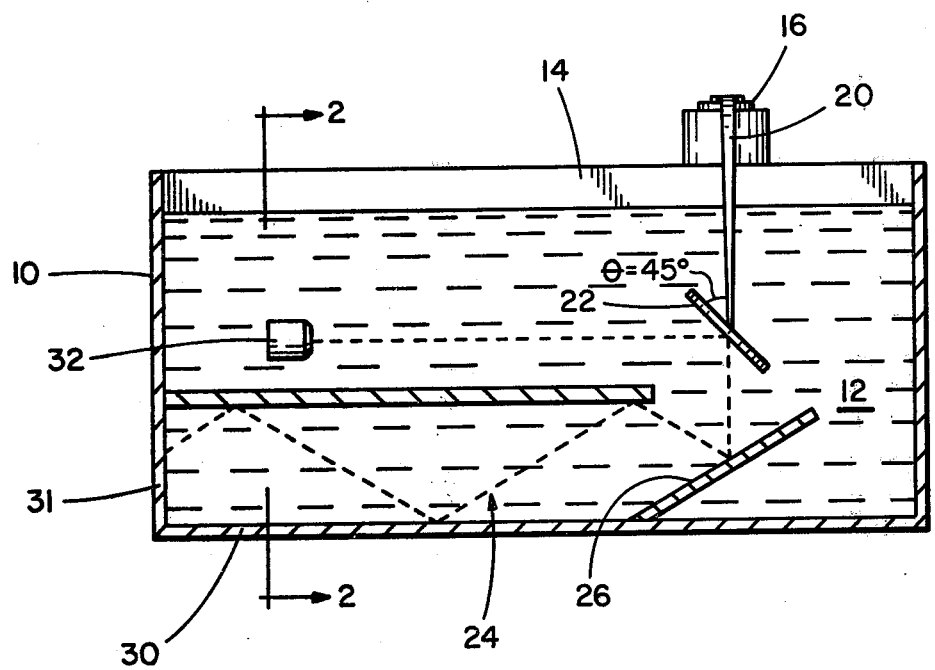
FIG. 1 is a sectional view through a water tank employed in the invention showing the essential detals thereof.
Figure 2:
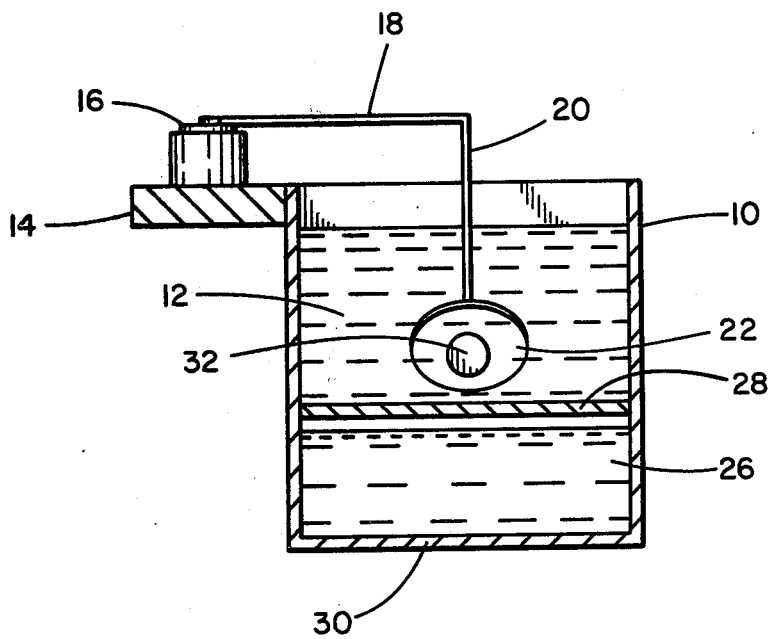
FIG. 2 is a sectional view along the lines 2—2 of FIG. 1.
Figure 3:
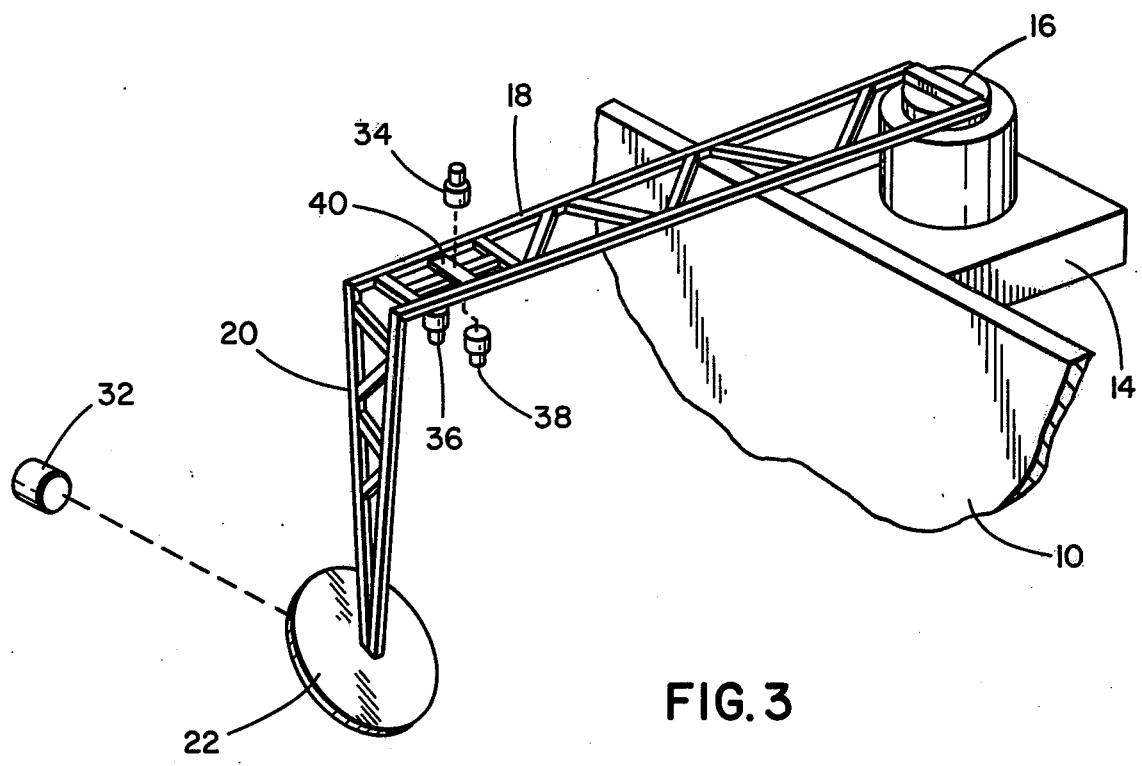
FIG. 3 is a perspective view of the meter movement arm and target vane useful in understanding the operation of the invention.

Referring now to FIG. 1, a measuring tank 10 filled with water is provided. Secured to the top 14 of the tank is a taut-band d'Arsonval meter movement 16. Attached to the movement is a radially extending arm 18 having a downwardly depending portion 20. Secured at the lower end of the portion 20 is the transducer target 22.

The target 22 consists of a hollow vane preferably formed of aluminum. The construction of the vane is selected so that it has essentially neutral buoyancy when disposed in the water bath. The target 22 is secured to the arm at an angle theta from the vertical, which angle is preferably 45°. The angle is selected for the purpose of reflecting the incident ultrasonic energy downwardly into an acoustic trap 24 provided at the bottom of the tank.

The trap includes a number of energy absorbing surfaces, including surfaces 26, 28 and the bottom and side walls 30 and 31. These surfaces may conveniently be formed of neoprene and will absorb well over 95 percent of the energy deflected into the trap thereby insuring that the only energy incident upon the target vane 22 will be directly from the transducer under test.

A transducer 32, to be tested, is placed in the bath at the location indicated in FIG. 1. It is positioned so that its energy output is directed at the target 22 along a substantially horizontal path as indicated by the dashed line.

As indicated previously, the arm and target assembly are movable within the bath. In the absence of a null circuit the energy of the transducer 32 impinging upon the target 22 would displace the target 22 from its initial position. The prior art utilized this displacement to determine the energy output of the transducer but in so doing undesirable errors are introduced. Accordingly, it is preferable to measure the energy without movement of the target from its original position by applying a restoring force to the arm which is equal but opposite to the force produced by the transducer energy striking the target.

For that purpose the present invention is provided with a light source 34 and a pair of electric eye detector elements 36 and 38. These elements are positioned at the null point of the target, that is, the position of the target when no energy is incident thereon. When the target and arm remain in the null position a blocking element 40 permits a small but equal amount of light to strike cells 36 and 38. If the arm starts to move from the null point, one of the electric eyes would receive more energy from the source 34 while the other cell would receive less. The cells are connected to the circuit illustrated in FIG. 4 for producing a restorative force of sufficient magnitude to maintain the desired null setting.

Figure 4:
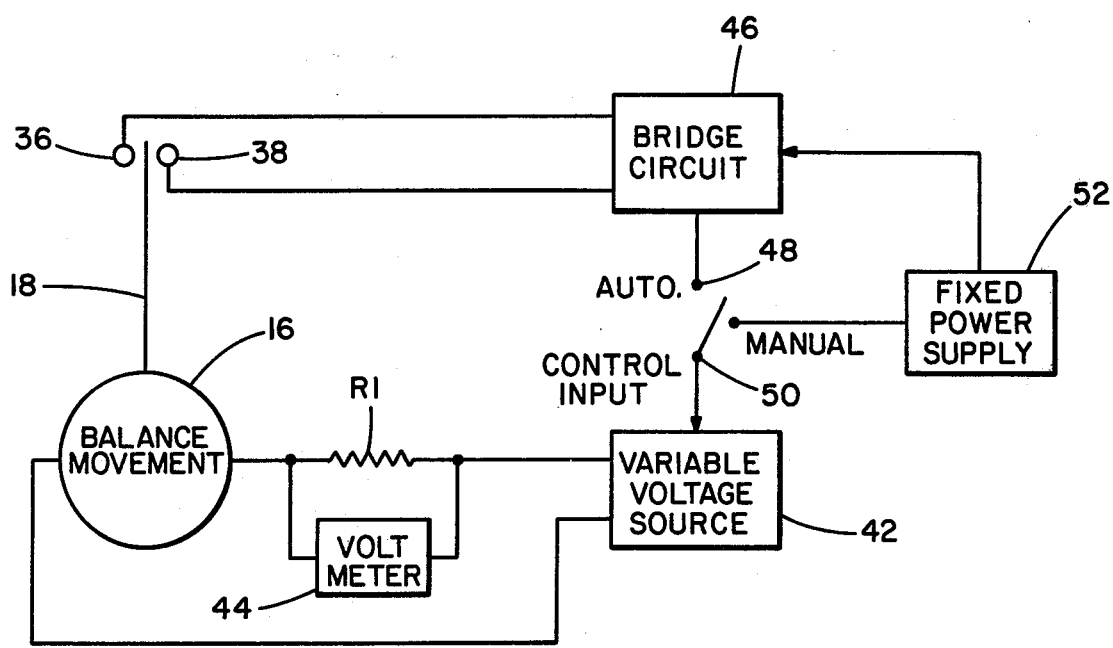
FIG. 4 is a schematic circuit diagram of the nulling circuit according to the invention.

Turning now to FIG. 4, the null circuit is illustrated in schematic form. The balance movement 16 is connected in circuit with and controlled by a variable voltage source 42. As is well known with respect to such balance movements the voltage applied thereto controls the deflection of the movement and, accordingly, the angular displacement of the arm 18 connected thereto. A resistor R1 is provided in series with the balance movement and voltage source. A volt meter 44 is connected thereacross to obtain the necessary readings to determine the transducer energy.

As shown schematically in the upper portion of FIG. 4, the electric eye cells 36 and 38 are positioned so that movement of the arm 18 in either direction away from the null point is effective for generating a voltage which is applied to a bridge circuit 46. In an automatic operating mode the output from the bridge circuit is applied via terminals 48 and 50 to control the operation of the variable voltage source 42. When the arm 18 is at the null point, bridge circuit 46 is balanced and voltage source 42 produces a constant voltage. If, however, the arm 18 begins to move from the null point, bridge 46 becomes unbalanced causing a change in voltage source 42 of a magnitude and polarity sufficient to produce a restorative force on the arm through the balance movement 16.

Alternately, the null point can be manually maintained by connecting the control input terminal 50 of the voltage source 42 to a fixed power supply 52 which can be manually changed, as necessary. This, however, is less desirable than automatic operation since the arm 18 will actually move and this introduces undesirable complications affecting the accuracy of the measurement including the movement of the water in the tank.

From the foregoing description the construction and operation of the invention should be apparent. For completeness, however, a brief operating description of the invention will be given. The transducer to be tested is placed in the bath and positioned as shown in FIG. 1. The test vane 22 is properly positioned to direct the incident ultrasonic energy into the trap 24. Before power is applied to the transducer the vane is located at the null point by adjusting the current applied to the movement 16 until the bridge 46 is balanced. Power is then applied to the transducer and the additional current required to maintain the arm at the null point is measured. This can be done either manually or automatically depending upon the mode selected.

The acoustic energy striking the target 22 can then be calculated from the torque-current conversion factor of the meter movement. The additional current required to maintain the null point is multiplied by the conversion factor to obtain the transducer power. The conversion factor can be empirically determined for each instrument by utilizing a transducer of known output. A typical conversion factor is 3.84 microamps per milliwatt of radiated power from a transducer.

By virtue of the use of the taut-band meter movement significant improvement is obtained over prior measuring devices where, for example, a jeweled fulcrum is employed which has a frictional coefficient orders of magnitude greater than the frictional coefficient of a taut-band meter movement. Similarly, because the present invention does not measure energy output as a function of vane displacement, errors due to the characteristics of the medium (water) in the tank are substantially eliminated. As a result the device has been found accurate in measuring ultrasonic energy down approximately to 300 microwatts.

While I have shown and described embodiments of this invention in some detail, it will be understood that this description and illustrations are offered merely by way of example, and that the invention is to be limited in scope only by the appended claims.

I claim:

1. Apparatus for measuring the power output of a transducer comprising:
    (a) a taut-band meter movement positionable as a function of applied electric current,
    (b) an arm connected to said meter movement for displacement therewith,
    (c) a target vane suspended from said arm, the energy to be measured being directed at said vane from said transducer,
    (d) means for applying current to said meter movement to position said arm at a null point or position,
    (e) means for altering the current applied to said meter movement, responsive to the force produced by said energy impinging on said target vane, to maintain said vane at the null point,
    (f) means for determining the magnitude of the current required to maintain the target vane at said null point before and during operation of said transducer, the change in current being a measure of transducer power.

2. Apparatus according to claim 1 wherein said apparatus further includes a tank filled with water, said target and transducer being disposed in the tank.

3. Apparatus according to claim 2 wherein said tank includes an acoustic trap for absorbing energy reflected from said target vane, said vane being positioned within said tank to reflect said energy into said trap.

4. Apparatus according to claim 2 wherein said meter movement is mounted to the top of said tank and said arm extends outwardly and downwardly therefrom into said tank.

5. Apparatus according to claim 1 wherein said target is a hollow circular vane of neutral buoyancy in water.

6. Apparatus according to claim 1 wherein said means for applying is a controllable, variable voltage source connected to said meter movement.

7. Apparatus according to claim 6 wherein said altering means includes:
    (a) electric eye means positioned adjacent said target vane in said tank for detecting movement of said target and producing signals indicative of target movement,
    (b) a bridge circuit receiving said signals and producing a control signal for said variable voltage source to alter the magnitude of the current applied to said meter movement sufficiently to maintain said vane at the null point.

8. Apparatus according to claim 1 wherein said altering means is a manually operable power supply connected to said applying means, said power supply controlling the output of said applying means to maintain the target vane at the null point.

9. Apparatus according to claim 1 wherein said altering means includes:

(a) electric eye means positioned adjacent said target vane in said tank for detecting movement of said target and producing signals indicative of target movement, (b) a bridge circuit receiving said signals and producing a control signal for altering the magnitude of the current applied to said meter movement by said applying means to maintain said vane at the null point.

10. Apparatus according to claim 1 wherein said detecting means includes a resistor in circuit between said meter movement and said applying means, and a volt meter connected across said resistor, whereby the current applied to said meter movement can be determined before and during operation of said transducer.

* * * * *